(12) United States Patent
Pedros et al.

(10) Patent No.: US 6,676,685 B2
(45) Date of Patent: Jan. 13, 2004

(54) ARTERIAL HOLE CLOSURE APPARATUS

(75) Inventors: Roberto Pedros, Seymour, CT (US); Keith Ratcliff, Newtown, CT (US); John C. Robertson, Chesire, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 46 days.

(21) Appl. No.: 09/883,427

(22) Filed: Jun. 18, 2001

(65) Prior Publication Data

US 2001/0044636 A1 Nov. 22, 2001

Related U.S. Application Data

(63) Continuation of application No. 09/503,510, filed on Feb. 14, 2000, now Pat. No. 6,248,124.
(60) Provisional application No. 60/121,114, filed on Feb. 22, 1999.

(51) Int. Cl.[7] .......................... A61B 17/04; A61B 17/36
(52) U.S. Cl. ........................... 606/213; 606/50
(58) Field of Search .................... 606/213, 40, 50, 606/51, 52

(56) References Cited

U.S. PATENT DOCUMENTS

| | | | |
|---|---|---|---|
| 5,318,589 A | * 6/1994 | Lichtman | 606/205 |
| 5,383,880 A | * 1/1995 | Hooven | 606/142 |
| 5,507,744 A | 4/1996 | Tay et al. | |
| 5,647,115 A | * 7/1997 | Slater et al. | 29/557 |
| 5,718,709 A | 2/1998 | Considine et al. | |
| 5,762,609 A | 6/1998 | Benaron et al. | |
| 5,810,810 A | * 9/1998 | Tay et al. | 606/50 |
| 5,827,296 A | 10/1998 | Morris et al. | |
| 5,836,905 A | 11/1998 | Lemelson et al. | |
| 5,836,945 A | 11/1998 | Perkins | |
| 5,916,233 A | 6/1999 | Chin | |
| 5,928,266 A | 7/1999 | Kontos | |
| 5,938,660 A | 8/1999 | Swartz et al. | |
| 5,954,731 A | * 9/1999 | Yoon | 606/144 |
| 5,964,782 A | 10/1999 | Lafontaine et al. | |
| 6,004,335 A | * 12/1999 | Vaitekunas et al. | 606/169 |
| 6,010,500 A | 1/2000 | Sherman et al. | |
| 6,063,085 A | 5/2000 | Tay et al. | |
| 6,099,550 A | * 8/2000 | Yoon | 606/205 |

* cited by examiner

*Primary Examiner*—Gary Jackson

(57) ABSTRACT

An arterial closure device for use following coronary catherization procedures to close arterial access openings through the arterial wall while permitting post operative flow through the artery includes a housing having proximal and distal ends, and defining a longitudinal axis, first and second arterial tissue everting members mounted adjacent the distal end of the housing and first and second jaw members mounted adjacent the first and second tissue engaging members. The first and second arterial tissue everting members are dimensioned for at least partial positioning within the arterial access opening in the arterial wall and are deployable in at least a radial outward direction relative to the longitudinal axis of the housing to engage respective opposed arterial tissue portions on opposed sides of the opening and move the tissue arterial portions to an everted condition thereof. The first and second jaw members are adapted for relative movement between an open position to facilitate positioning about the arterial tissue portions in the everted condition and a closed position to at least partially draw the arterial tissue portions together to an at least partial approximated condition. An electrode is associated with at least one of the first and second jaw members and arranged to contact the respective arterial tissue portions. The electrode is adapted to be connected to a radio frequency energy source whereby energy is transmitted through the electrode to thermally fuse the arterial tissue positions between the first and second jaw members to substantially close the opening. Preferably, an electrode is associated with each of the first and second jaw members. Each electrode nay be configured as a bipolar electrode.

25 Claims, 5 Drawing Sheets

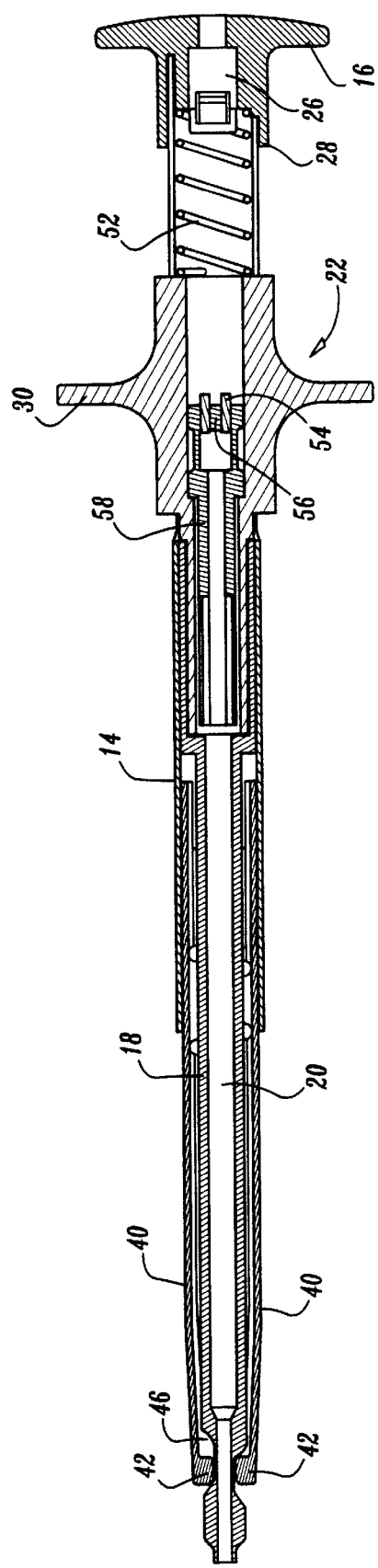
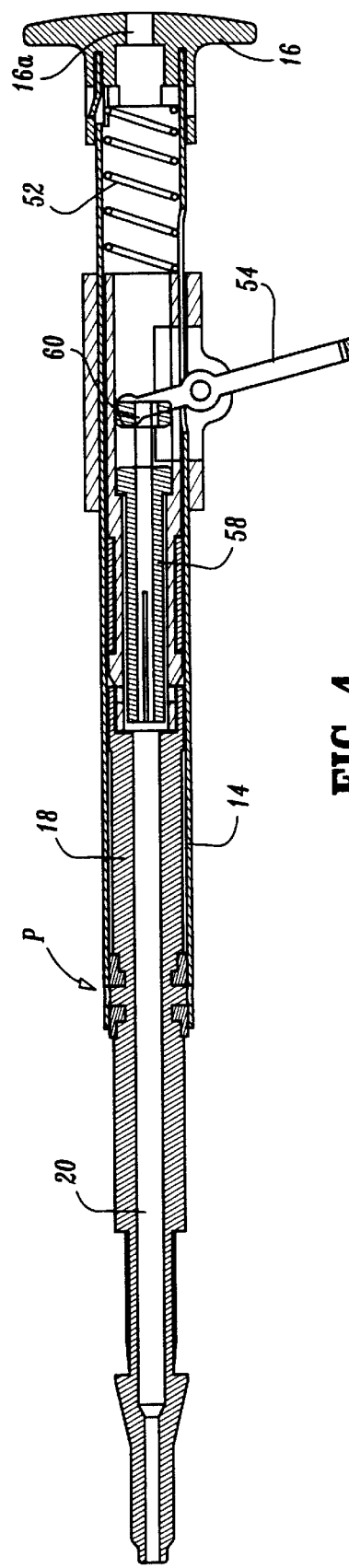

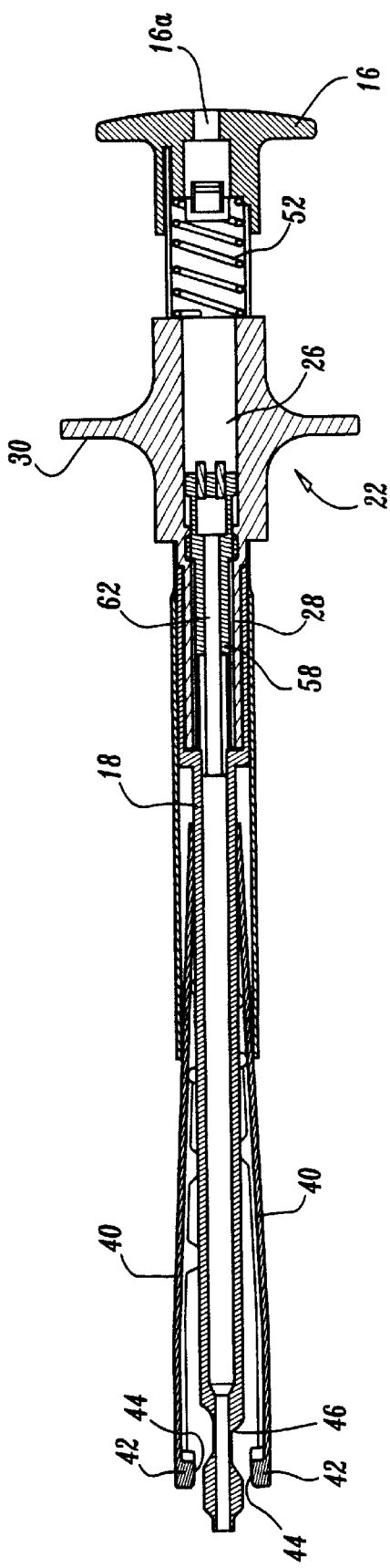
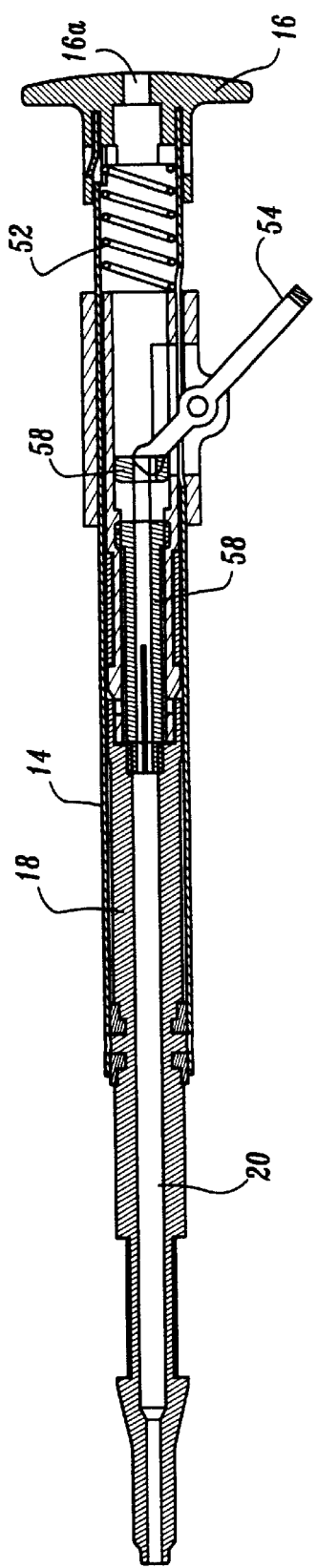
FIG. 5
FIG. 6

ARTERIAL HOLE CLOSURE APPARATUS

This Appln is a con't of Ser. No. 09/503,510 filed Feb. 14, 2000 now U.S. Pat. No. 6,248,124 and claims benefit of Prov. No. 60/121,114 filed Feb. 22, 1999.

BACKGROUND

1. Technical Field

The present disclosure relates to an arterial closure device used following a coronary catherization procedure for closing an arterial access opening formed through the arterial wall while permitting post operative blood flow through the artery.

2. Background of the Related Art

When performing a catheterization procedure such as for example, an angiography or angioplasty, a sharpened hollow needle is first percutaneously introduced into the vascular system. A guide wire is then inserted through the hollow needle and into the lumen of a selected blood vessel. Subsequently, the needle is removed and a dilator and/or introducer is fed into the vessel along the guide wire. The guide wire is then removed and a suitable catheter is fed through the lumen of the introducer and advanced through the vascular system until the working end thereof is positioned at the operating site. At the conclusion of the catheterization procedure, the catheter is withdrawn, followed by removal of the dilator and/or introducer.

At this point in the procedure, the vessel puncture must be sealed to stem the flow of blood therethrough. Generally, this procedure is extremely difficult due to the nature of the vessel tissue and to the presence of a blood thinning agent which is typically administered prior to the catheterization. A common method of closing the wound is to maintain external pressure over the vessel until the puncture naturally seals. This method of puncture closure typically takes about thirty minutes, with the length of time usually being greater if the patient is hypertensive or anticoagulated. When hand pressure is utilized, it can be uncomfortable for the patient and can use costly professional time on the part of the hospital staff. Other pressure application techniques, such as pressure bandages, sandbags or clamps, have been employed, but these techniques also require the patient to remain motionless for an extended period of time and the patient must be closely monitored to ensure the effectiveness.

Other devices have been disclosed that plug or otherwise provide an obstruction in the area of the puncture. See, for example, U.S. Pat. Nos. 4,852,568 and 4,890,612, wherein a collagen plug is disposed in the blood vessel opening. When the plug is exposed to body fluids, it swells to create a block for the wound in the vessel wall. A potential problem of plugs introduced into the vessel is that plug particles may break off and float downstream to the point where they may lodge in a smaller vessel, causing an infarct to occur. Collagen material also acts as a nidus for platelet aggregation and, therefore, can cause intraluminal deposition of a hemostatic agent, thereby creating the possibility of a thrombosis at the puncture site. Other plug-like devices are disclosed, for example, in U.S. Pat. Nos. 5,342,393; 5,370, 660; and 5,411,520.

U.S. Pat. Nos. 5,417,699 and 5,527,322 each to Klein et al. discloses a suture applying device for the percutaneous suturing of a vascular puncture site. These devices include a shaft which carries a pair of needles at its distal end. The needles are joined by a length of suture. The shaft is used to both introduce the needles within the lumen of the vessel and to draw the needle back through the vessel wall leaving a loop of suture behind to close the puncture site.

U.S. Pat. No. 5,810,810 to Tay et al. discloses an apparatus for closing and sealing a vascular puncture utilizing heat to thermally fuse the vascular tissue. The Tay '810 device includes a vessel balloon occluder which is introduced within the lumen of the vessel to occlude the opening and a forceps which are intended to grasp the vascular tissue surrounding the opening. The forceps serve as electrodes and are energized by radiofrequency energy to thermally fuse the tissue grasped therebetween.

SUMMARY

Accordingly, the present invention is directed to an arterial closure device used following coronary catherization procedures to close arterial access openings through the arterial wall while permitting post operative flow through the artery. In the preferred embodiment, the apparatus includes a housing having proximal and distal ends, and defining a longitudinal axis, first and second arterial tissue everting members mounted adjacent the distal end of the housing and first and second jaw members mounted adjacent the first and second arterial tissue engaging members. The first and second arterial tissue everting members are dimensioned for at least partial positioning within the arterial access opening in the arterial wall and are deployable in at least a radial outward direction relative to the longitudinal axis of the housing to engage respective opposed arterial tissue portions on opposed sides of the opening and move the arterial tissue portions to an everted condition thereof. The first and second jaw members are adapted for relative movement between an open position to facilitate positioning about the arterial tissue portions in the everted condition and a closed position to at least partially draw the arterial tissue portions together to an at least partial approximated condition. An electrode is associated with at least one of the first and second jaw members and arranged to contact the respective arterial tissue portions. The electrode is adapted to be connected to a radiofrequency energy source whereby energy is transmitted through the electrode to thermally fuse the arterial tissue positions between the first and second jaw members to substantially close the opening. Preferably, an electrode is associated with each of the first and second jaw members. Each electrode may be configured as a bipolar electrode.

Each arterial tissue everting member includes a distal memory portion comprising a shape memory material, the distal memory portion being adapted to assume a normal unstressed condition upon deployment to engage and move the arterial tissue portions to the everted condition. The normal unstressed condition of each arterial tissue everting member may be a general hook-shaped configuration. Preferably, the distal memory portions of the tissue everting members define general hook-shaped configurations in diametrical opposed relation and extending in radial opposite directions.

A manually operable deployment member may be operatively connected to the arterial tissue everting members, and movable to deploy the tissue everting members. An actuator is operatively connected to the first and second jaw members with the actuator movable to cause corresponding movement of the first and second jaw members between the open and closed positions.

The apparatus may include an elongated shaft at least partially disposed within the housing. The elongated shaft has camming structure which cooperates with corresponding camming structure of the first and second jaw members to move the jaw members between the open and closed positions.

BRIEF DESCRIPTION OF THE DRAWINGS

Preferred embodiments of the disclosure are described herein with reference to the drawings wherein:

FIGS. 3–4 are side cross-sectional views of the apparatus in an unactuated position;

FIGS. 5–6 are side cross-sectional views of the apparatus in an actuated position.

DETAILED DESCRIPTION OF THE PREFERRED EMBODIMENTS

Figure 1:
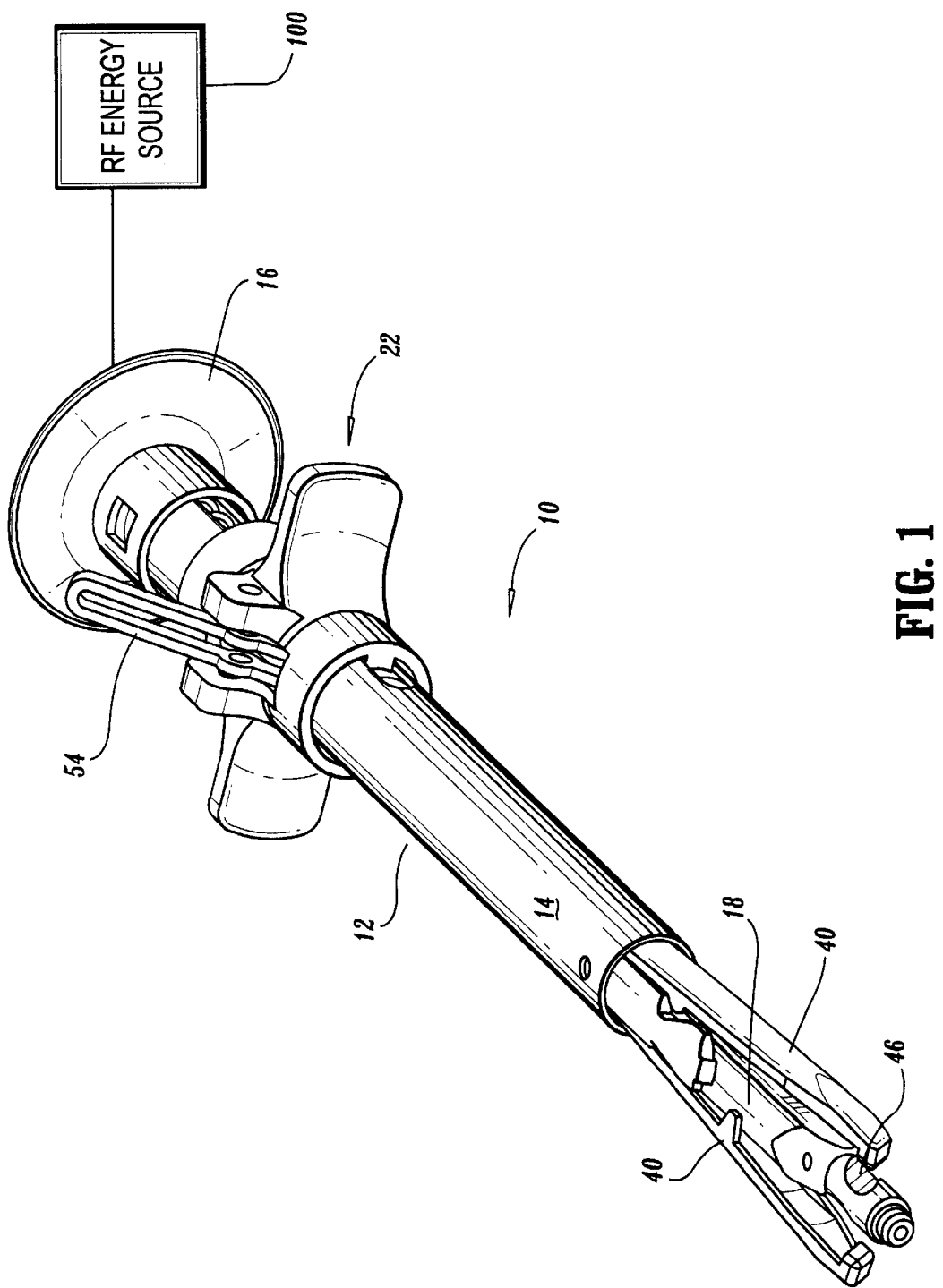
FIG. 1 is a perspective view of the surgical apparatus for facilitating closure of an arterial access opening in the arterial wall in accordance with the principles of the present disclosure.

In general, the object of the apparatus is to close an arterial access opening in an arterial wall following a coronary catheterization procedure, to stem the flow of blood through the opening while permitting post operative blood flow through the artery. In the drawings and in the description which follows, the term "proximal", as is traditional, will refer to that end of the apparatus, or component thereof, which is closer to the operator, while the term "distal" will refer to that end of the apparatus, or component thereof, which is more remote from the operator.

Referring now in detail wherein like reference numerals identify similar components throughout the several views, FIG. 1 illustrates in perspective the apparatus in accordance with the principles of the present disclosure. Arterial closure apparatus 10 is configured to close an arterial access opening in an arterial wall. In achieving this objective, arterial apparatus 10 has incorporated therein several mechanisms; namely, 1) an arterial tissue everting mechanism which everts the tissue portions on each side of the arterial opening such that the arterial portions are exposed and arranged at a desired orientation; and 2) an arterial tissue approximating mechanism which draws the everted arterial portions to a general closed approximated position and maintains a predetermined degree of pressure on the arterial portions. A thermal treatment mechanism supplies thermal energy across the approximated everted arterial tissue portions for a desired predetermined time and intensity to effectuate complete thermal fusion of the everted arterial portions.

Figure 2:
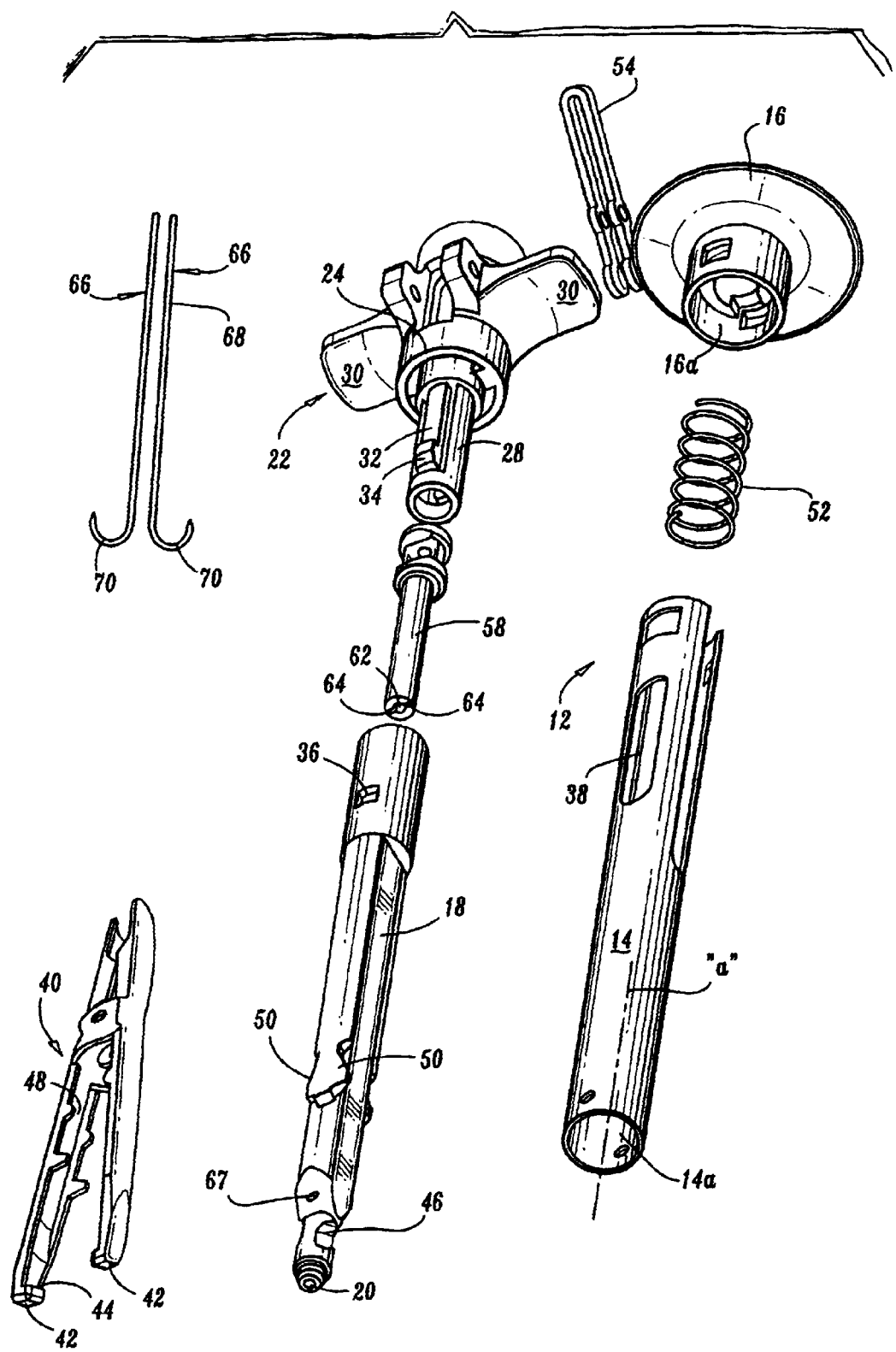
FIG. 2 is a perspective view with parts separated of the apparatus of FIG. 1.

Referring now to FIGS. 2–4, in conjunction with FIG. 1, the components of apparatus 10 will be discussed in detail. Apparatus 10 includes main housing 12 which accommodates the mechanisms discussed above. Main housing 12 includes outer sleeve 14 and circular flange 16 which is fixedly mounted to the proximal end of outer sleeve 14. Outer sleeve 14 defines longitudinal axis "a" and has a longitudinal opening 14a extending completely therethrough. Circular flange 16 also defines longitudinal opening 16a (FIG. 3) in general alignment with the opening of the outer sleeve 14. Circular flange 16 may be fixedly mounted to outer sleeve 14 by any conventional means including adhesives, snap-groove fit, bayonet coupling etc. Outer sleeve 14 and circular flange 16 may be fabricated from any suitable rigid material including stainless steel titanium, or a rigid polymeric material. Housing 12 further includes central elongated shaft 18 disposed within outer sleeve 14 and mounted for relative longitudinal movement therewithin. Central shaft 18 defines a central lumen 20 dimensioned to receive a guide wire. The remaining features and components of housing 12 will be discussed in greater detail below.

With continued reference to FIGS. 2–4, the components of the arterial tissue approximating mechanism will be discussed. The tissue approximating mechanism includes manually operable actuator 22 which is mounted to outer sleeve 14 in a manner to permit relative longitudinal movement of the actuator 22 and the sleeve 14. Actuator 22 includes main portion 24 defining a central lumen 26 and tubular portion 28 extending from the main portion 24. Main portion 24 defines a pair of manually engageable finger grips 30 extending radially outward from the main portion 24. Finger grips 30 are positioned to be engaged by the user's fingers during use while the user's palm engages circular flange 16. Tubular portion 28 of actuator 22 possesses a pair of resilient legs 32 (FIG. 2) extending in a general longitudinal direction. Resilient legs 32 have radially outwardly extending resilient tabs 34 adjacent their distal ends which are received within corresponding slots 36 of elongated shaft 18 in a snap fit manner to connect the two components. With this arrangement, actuator 22 is longitudinally fixed with respect to elongated shaft 18. Tabs 34 of actuator legs 32 are also accommodated within longitudinal slots 38 of outer sleeve 14 to operatively connect these components. Tabs 34 of actuator legs 32 are capable of sliding within slots 38 to thereby provide relative movement between outer sleeve 14 and actuator 22

With reference still to FIGS. 2–4, the arterial tissue approximating mechanism further includes a pair of jaw members 40. Jaw members 40 are connected to outer sleeve 14 at location "P" (FIG. 4) through a pivot pin arrangement (not shown) and thus are longitudinally fixed with respect to the sleeve 14. Jaw members 40 are adapted to move or pivot from the closed or approximated position depicted in FIG. 3 to the open position depicted in FIG. 5. Jaw members 40 each define an arterial tissue contacting portion 42 adjacent their respective distal ends. Arterial tissue contacting portion 42 each depend radially inwardly and define a planar tissue contacting surface 44. In the closed position of jaw members 40 depicted in FIG. 3, tissue contacting portions 42 are received within corresponding recesses 46 of elongated shaft 18 to define the reduced profile shown. Jaw members 40 further define first and second interior camming surfaces 48. Camming surfaces 48 engage corresponding camming surfaces 50 of elongated shaft 18 to cause the jaw members 40 to assume the open position depicted in FIG. 5 as will be discussed.

The tissue approximating mechanism is normally biased to the closed position of FIG. 3 by coil spring 52. More particularly, coil spring 52 is in engagement with flange 16 of housing 12 and actuator 22 and serves to normally bias the flange 16 and the actuator 22 in opposite directions, thus biasing outer sleeve 14 and jaw members 40 in the opposite (proximal) direction relative to elongated shaft With continued reference to FIGS. 2–4, the arterial tissue everter mechanism will be discussed. The arterial tissue everter mechanism includes a manually operative lever 54 pivotally mounted to actuator 22 about pivot pin 56 and drive tube 58 which is operatively connected to operative lever 54 through pin 60. With this arrangement, pivotal movement of lever 54 causes drive tube 58 to longitudinally translate. Drive tube 58 includes central opening 62 which receives guide wire "w" and outer longitudinal slots 64 (FIG. 2) defined in the outer wall of the drive tube 58. With reference to FIG. 2, the tissue everter mechanism further includes a pair of arterial tissue everting members 66. In FIGS. 1 and 3–6, everting members 66 are not shown/visible. Tissue everting members 66 are accommodated within longitudinal slots 64 of drive tube 58 and extend distally with elongated shaft 16 through a pair of longitudinal slots 67 (FIG. 2) defined within the outer wall of the elongated shaft 16. Each tissue everting member 66 is fixed to drive tube 58 by conventional means to thereby longitudinally move with the drive tube 58, but, is capable of sliding within slots 67 of elongated shaft 16. Each everting member 66 defines a generally straight proximal portion 68 and a curved distal portion 70. Tissue everting members 66 are fabricated from a shape memory material such as Tinel™. In the normal unstressed condition of tissue everting members, the distal portions 70 assume the opposed hook or J-shaped configuration shown. In this configuration, the distal portions 70 engage the interior arterial portions to surrounding the vessel opening to evert the tissue portions to a desired orientation. The extreme distal end of each tissue everting member is relatively sharp to facilitate engagement with the vessel portion. In the non-deployed position, tissue everting members 66 are received within longitudinal slots 67 of elongated shaft 18 whereby the curved distal portion is straightened by the biasing affects of the elongated shaft With reference to FIG. 1, in conjunction with FIG. 3, the thermal treatment energy source 100 is shown in block diagram. The thermal treatment energy source does not form part of the invention as a variety of different generators can be utilized to apply thermal energy to the tissue. Preferably, the energy source includes an RF energy source which is capable of supplying RF energy at a frequency ranging between 10 Khz to 300 GHz. One suitable RF energy source is the WeO Fich LT made by Mentor U&O, Inc. Another suitable power source is the Valley Lab Force FX an Force EZ generator. Other RF generators suitable for this use are envisioned as well such as those enumerated in U.S. Pat. No. 5,810,810. The generator selected may depend on the intended use requirements of the surgeons. Also, energy can be supplied at other frequency ranges other than radiofrequency, as well. The energy source needs to be in electrical contact with jaw member 40. In the illustrated embodiment, this is achieved through conventional leads with electrodes associated with jaw members 40. In one embodiment, the contacting surface 44 of each jaw member 40 functions as the RF electrode and is electrically connected through lead lines (not shown) to the RF power source. Preferably, the RF electrodes are each configured as bipolar electrodes to transmit RF energy therebetween. A monopolar arrangement is envisioned as well. It is also envisioned the jaw members 40 may be conductive with the extreme tissue contacting portion 42 left uninsulated to transmit the thermal energy.

OPERATION OF THE APPARATUS

The operation of surgical apparatus 10 will now be discussed. Apparatus 10 is used to close an arterial access opening in an arterial wall subsequent to a coronary catherization procedure while permitting blood flow through the artery. The initial position of apparatus 10 is best depicted in FIGS. 3–4.

Figure 7A:
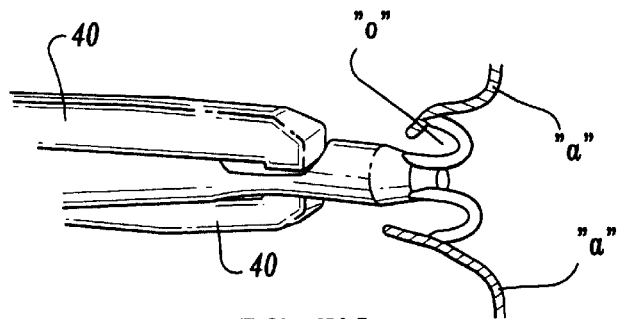
FIGS. 7A–7D are perspective views depicting the sequence of movement of the arterial tissue everters members and the jaw members during movement of the apparatus to the actuated position.

Surgical apparatus 10 is then advanced along a guide wire which had been previously introduced in connection with the angioplasty procedure to access the surgical site. The guide wire is received within the central lumen 20 of elongated shaft 18 and extends proximally within opening 62 of drive tube 58 where it passes through the opening 16a of flange 16. Apparatus 10 is advanced along the guide wire until the distal hub portion is received within the opening of the arterial wall and at least partially disposed within the vessel lumen. Thereafter, lever 54 is pivoted from its initial position of FIG. 3 to its position of FIG. 5 to cause corresponding movement of drive tube 58 and tissue everting members 66 to advance within slots of elongated shaft 18. Upon deployment from elongated shaft 18, distal portions 70 of tissue everting members 66 assume their normal unstressed condition, i.e., the J-shaped configuration shown in FIG. 7A. In this position, the extreme distal ends of the distal hook portion 70 engage the interior arterial wall portions "a" on each side of the opening "o" to essentially draw the wall portions "a" upwardly to an everted position shown in the Figure. It is noted that at this point the surgeon may slightly "pull-back" the apparatus to exaggerate the everted condition of the arterial portions "a" if desired.

Figure 7B:
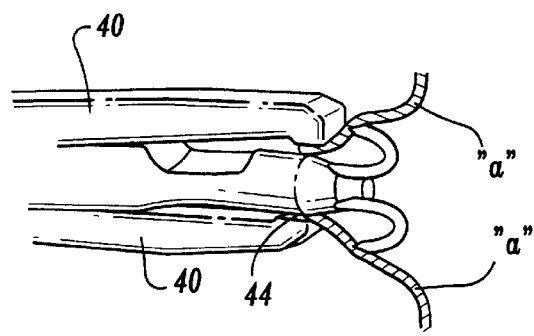
Figure 7C:
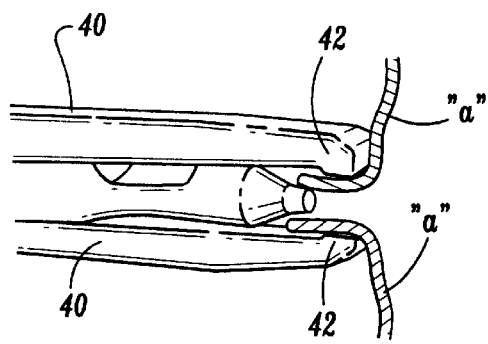
Figure 7D:
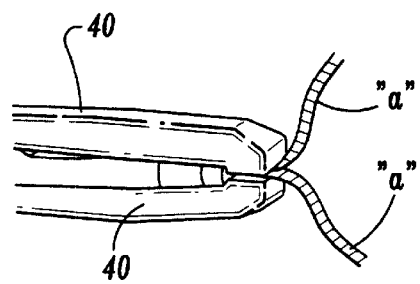

With the arterial portions "a" properly everted, the surgeon thereafter pushes on flange 16 to cause drive sleeve 14 and jaw members 40 to distally move. During such movement, camming surfaces 50 of elongated shaft IS engage camming surfaces 48 of jaw members 40 to cause the jaw members 40 to pivot outwardly to the open position depicted in FIGS. 5 and 7B. In the open position, the jaw members 40 are positioned about the everted wall portions "a" as depicted in FIG. 7C. Thereafter, jaw members 40 are closed by either releasing actuator 22 or flange 16, or a combination of each movement, to cause the jaw members 40 to close or clamp tightly down on the everted wall portions as shown in FIG. 7D.

With the everted wall portions "a" in their proper everted positions clamped by jaw members 40, the RF energy source is energized to cause current to be emitted through the arterial tissue captured by the jaw members 40. Preferably, the energy is for a sufficient period of time and at an appropriate level to thermally treat and fuse the tissue portions to each other. Once fused, the access opening is closed while blood flow through the artery continues. If desirable, the RF energy source may incorporate various means to detect when treatment has been successfully accomplished or when undesired treatment of neighboring tissue areas occurs. Such means may include temperature sensor means, impedance measurement means, etc. appreciated by one skilled in the art. Other types of feedback mechanism or circuits can optimally be provided as part of the energy source if monitoring of specific parameters is desired by the surgeon. It is noted that the clamping pressure provided by jaw members 40 ensures that the tissue portions are approximated thereby facilitating the fusion process. Upon completion, the apparatus may then be removed from the surgical site along the guide wire.

Although certain embodiments and examples have been used to illustrate and describe the apparatus of the present invention, it is intended that the scope of the invention not be limited to the specific embodiments of the apparatus set forth herein. The scope of the invention is to be defined by the claims which follow.

What is claimed is:

1. An apparatus for closing a vascular puncture, which comprises:

a housing having proximal and distal ends and defining a longitudinal axis;

at least two tissue engaging members disposed adjacent the distal end of the housing, the tissue engaging members deployable within the vascular puncture and cooperating to engage vascular tissue portions adjacent the vascular puncture, and being dimensioned and configured to arrange the vascular tissue portions to a desired orientation thereof; and at least two outer jaw members positioned radially outwardly of the tissue engaging members and adapted for relative movement from an open position to facilitate positioning of the jaw members with respect to the vascular tissue portions when in the desired orientation, to a closed position to at least partially approximate the tissue portions, at least one of the jaw members having a thermal transmitting portion adapted to connect to an electrical energy source to transmit thermal energy to thermally fuse the approximated vascular tissue portions.

2. The apparatus according to claim 1 wherein each jaw member includes a thermal transmitting portion adapted to connect to the electrical energy source.

3. An apparatus for closing a vascular puncture, which comprises:

a housing having proximal and distal ends;

at least two tissue engaging members disposed adjacent the distal end of the housing, the tissue engaging members deployable within the vascular puncture to engage vascular tissue portions adjacent the vascular puncture, and being dimensioned and configured to arrange the vascular tissue portions to a desired orientation thereof;

each tissue engaging member having a distal portion comprising a shape memory material adapted to assume a normal unstressed condition upon deployment to be in position to engage the vascular tissue portions to arrange the vascular tissue portions to the desired orientation; and at least two jaw members mounted adjacent the tissue engaging members and adapted for relative movement from an open position to facilitate positioning of the jaw members with respect to the vascular tissue portions when in the desired orientation, to a closed position to at least partially approximate the tissue portions, at least one of the jaw members having a thermal transmitting portion adapted to connect to an electrical energy source to transmit thermal energy to thermally fuse the vascular tissue portions.

4. The apparatus according to claim 3 wherein the distal portion defines a general J-shape.

5. The apparatus according to claim 3 including an elongated shaft at least partially disposed in the housing.

6. The apparatus according to claim 5 wherein the tissue engaging members are at least partially disposed within the elongated shaft, the tissue engaging members adapted for longitudinal movement relative to the elongated shaft between a first position wherein the distal portion of each tissue engaging member is in a stressed condition confined within the elongated shaft, and a second position wherein the distal portion of each tissue engaging member is exposed from the elongated shaft to assume the normal unstressed condition thereof.

7. The apparatus according to claim 6 wherein the elongated shaft includes a longitudinal slot for accommodating the tissue engaging members.

8. The apparatus according to claim 7 wherein the jaw members are adapted for longitudinal movement relative to the elongated shaft to move between the open and closed positions.

9. The apparatus according to claim 8 wherein the elongated shaft includes camming structure which corresponds with corresponding camming structure of the jaw members to move the jaw members to the open position.

10. An apparatus for closing a vascular puncture, which comprises:

a housing having proximal and distal ends;

at least two tissue engaging members disposed adjacent the distal end of the housing, the tissue engaging members deployable within the vascular puncture to engage vascular tissue portions adjacent the vascular puncture, and being dimensioned and configured to arrange the vascular tissue portions to a desired orientation thereof;

at least two jaw members mounted adjacent the tissue engaging members and adapted for relative movement from an open position to facilitate positioning of the jaw members with respect to the vascular tissue portions when in the desired orientation, to a closed position to at least partially approximate the tissue portions, at least one of the jaw members having a thermal transmitting portion adapted to connect to an electrical energy source to transmit thermal energy to thermally fuse the vascular tissue portions; and a thermal energy source connected to the thermal transmitting portion of the one jaw member.

11. The apparatus according to claim 10 wherein the thermal energy source is a radio frequency energy source.

12. An apparatus for closing a vascular opening in a vascular wall, which comprises:

a housing having proximal and distal ends, and defining a longitudinal axis;

first and second tissue engaging members mounted adjacent the distal end of the housing, the first and second tissue engaging members being dimensioned for at least partially positioning within the vascular opening in the vascular wall, the first and second tissue engaging members being deployable from the housing to engage and expose internal vascular tissue portions adjacent the vascular opening and to arrange the vascular tissue portions at a predetermined orientation;

first and second jaw members mounted adjacent the first and second tissue engaging members, the first and second jaw members adapted for relative movement to engage the vascular tissue portions in the predetermined orientation and to substantially approximate the internal vascular tissue portions, at least one of the first and second jaw members having a thermal transmitting region, adapted for communication with a thermal energy source whereby thermal energy is transmitted through the thermal transmitting region to thermally fuse the approximated tissue portions between the first and second jaw members to substantially close the vascular opening;

a manually operable deployment member operatively connected to the first and second tissue engaging members, and being movable to deploy the first and second tissue engaging members; and an actuator operatively connected to the first and second jaw members, the actuator movable to cause corresponding movement of the first and second jaw members.

13. An apparatus for closing a vascular opening in a vascular wall, which comprises:

a housing having proximal and distal ends, and defining a longitudinal axis;

first and second tissue engaging members mounted adjacent the distal end of the housing, the first and second tissue engaging members being dimensioned for at least partially positioning within the vascular opening in the vascular wall, the first and second tissue engaging members being deployable from the housing to engage and expose internal vascular tissue portions adjacent the vascular opening;

each tissue engaging member includes a distal memory portion comprising a shape memory material, the distal memory portion being adapted to assume a normal unstressed condition upon deployment to engage the vascular tissue portions;

first and second jaw members mounted adjacent the first and second tissue engaging members, the first and second jaw members adapted for relative movement to substantially approximate the internal vascular tissue portions subsequent to deployment of the first and second tissue engaging member, at least one of the first and second jaw members having a thermal transmitting region, adapted for communication with a thermal energy source whereby thermal energy is transmitted through the thermal transmitting region to thermally fuse the tissue portions between the first and second jaw members to substantially close the vascular opening;

a manually operable deployment member operatively connected to the first and second tissue engaging members, and being movable to deploy the first and second tissue engaging members; and an actuator operatively connected to the first and second jaw members, the actuator movable to cause corresponding movement of the first and second jaw members.

14. The apparatus according to claim 13 wherein an electrode is associated with each of the first and second jaw members.

15. The apparatus according to claim 14 wherein each electrode is configured as a bipolar electrode.

16. The apparatus according to claim 13 including an elongated shaft at least partially disposed in the housing.

17. The apparatus according to claim 16 wherein the tissue engaging members are at least partially disposed within the elongated shaft, the tissue engaging members adapted for longitudinal movement relative to the elongated shaft between a first position wherein the distal memory portion of each tissue engaging member is in a stressed condition confined within the elongated shaft, and a second position wherein the distal memory portion of each tissue engaging member is exposed from the elongated shaft to assume the normal unstressed condition thereof.

18. A method of closing a vascular opening within a vascular organ, comprising the steps of:

introducing a vascular closure apparatus at least partially within a vascular opening in a vascular organ;

deploying tissue engaging members of the apparatus within the vascular organ;

engaging internal vascular tissue portions adjacent the vascular opening with the tissue engaging members;

approximating the internal vascular tissue portions; and conducting electrical energy between the jaw members to at least partially fuse the internal vascular tissue portions.

19. The method according to claim 18 wherein the tissue engaging members comprise a shape memory material, and wherein the step of deploying includes permitting the tissue engaging members to assume a normal unstressed condition so as to be in position to engage the internal vascular tissue portions to arrange the internal vascular tissue portions at a desired orientation.

20. The method according to claim 19 wherein the step of approximating includes engaging the internal vascular tissue portions when in the desired orientation with jaw members of the apparatus and moving the jaw members to an approximated position.

21. The method according to claim 20 wherein the step of conducting electrical energy comprises transmitting radio frequency energy from at least one of the jaw members.

22. An apparatus for closing an opening in tissue, which comprises:

an elongated shaft having proximal and distal ends, and defining a longitudinal axis;

first and second tissue engaging members at least partially disposed in the elongated shaft, each tissue engaging member having a distal engaging portion defining a normal unstressed arcuate condition, the tissue engaging members being adapted for longitudinal movement relative to the elongated shaft to be deployed within the opening in tissue whereby the distal engaging portions engage the tissue portions surrounding the opening to arrange the tissue portions at a desired orientation; and first and second jaw members mounted about the elongated shaft and adapted for relative movement between an open position to receive the tissue portions and a closed position to approximate the tissue portions, at least one of the jaw members having a thermal transmitting portion adapted to connect to an electrical energy source to thermally fuse the tissue portions.

23. The apparatus according to claim 22 wherein the elongated shaft includes camming surfaces to cooperate with camming surfaces of the jaw members to move the jaw members from the open to the closed positions thereof.

24. The apparatus according to claim 22 wherein the jaw members are adapted for longitudinal movement relative to the elongated shaft to move between the open and closed positions thereof.

25. The apparatus according to claim 22 wherein the first and second tissue engaging members are adapted for longitudinal movement between a first position wherein the distal engaging portions are at least partially disposed in a stressed condition within the elongated shaft and a second position wherein the distal engaging portions are deployed to assume the normal unstressed arcuate condition thereof.

* * * * *